United States Patent [19]

Chamberlin, Sr.

[11] Patent Number: Plant 5,874

[45] Date of Patent: Feb. 10, 1987

[54] PEACH TREE—DAVID SUN

[75] Inventor: Thomas O. Chamberlin, Sr., Visalia, Calif.

[73] Assignee: Metzler Investments and Metropolitan Life Insurance Company, Del Rey, Calif.

[21] Appl. No.: 739,014

[22] Filed: May 29, 1985

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Worrel & Worrel

[57] ABSTRACT

A peach tree, denominated "David Sun", producing very firm yellow fleshed cling fruit having a skin of very high dark red to bright yellow color ready for harvest about June 1 and reaching full maturity about June 4.

1 Drawing Figure

BACKGROUND OF THE VARIETY

The present invention relates to a new and distinct variety of peach tree, denominated "David Sun", which is a newly found seedling of the "June Lady" peach tree having cling fruit of very high dark red to bright yellow color, very firm yellow flesh and good flavor reaching picking ripeness about June 1 and full maturity about June 4 at Del Rey, Calif.

A variety of attributes can enhance the commercial value of tree fruit. Such characteristics as early ripening, bright skin color, large size, good flavor, low acidity, tight flesh, keeping quality and the like may all play a part in determining the market value of tree fruit. It is, however, quite unusual for tree fruit to excel in more than a few such characteristics.

There are other characteristics which are more directly related to the commercial value of the trees themselves in that the production of the tree fruit is made easier. Thus, such characteristics as tree size, vigor of growth, the holding quality of the fruit on the trees, resistance to breakdown in the fruit and in the trees themselves, ripening dates, storage and shipping quality and the like may make certain varieties of trees more desirable than others. Again, it is quite unusual for tree varieties to excel in more than a few such characteristics.

The variety of peach tree of the present invention is distinct from other varieties of peach tree known to the applicant in that it excels in a prodigious number of these characteristics. The fruit ripens early and holds very well on the tree, as well as having a long storage life. The fruit is of the cling type and will not breakdown on its suture or apex. Furthermore, the fruit is distinctive in that it has a very high color with very firm yellow flesh having good flavor and low acid taste.

ORIGIN AND ASEXUAL REPRODUCTION OF THE NEW VARIETY

The new variety of peach tree of the present invention was discovered by me in 1977 and is a newly found seedling of the "June Lady" peach tree. Seeds of the "June Lady" peach tree were planted in the nursery of H. P. Metzler & Sons at 5286 South Del Rey Avenue, Del Rey, Calif. 93616 in 1975. The first fruit of the variety of the present invention was observed in 1977 and its distinctive characteristics discovered at that time.

The new variety was asexually propagated under my direction at H. P. Metzler & Sons in 1978 by grafting a number of seedlings with scions from the newly discovered seedling. The grafted seedlings were in 1978 planted in a test nursery of H. P. Metzler & Sons at Del Rey, Calif. The seedlings of the new variety were observed in the test nursery over several growing seasons and tree and fruit characteristics resulting from such asexual reproduction proved to be identical to those of the original seedling of the new variety.

SUMMARY OF THE NEW VARIETY

The new variety of peach tree of the present invention is characterized by its cling fruit having a skin of very high dark red to bright yellow color, very firm yellow flesh and good flavor reaching picking ripeness about June 1 and full maturity about June 4 at Del Rey, Calif., the fruit being still further characterized by its excellent holding quality on the tree and by its excellent storage and shipping quality.

BRIEF DESCRIPTION OF THE DRAWING

The accompanying drawing is a color photograph of four mature fruit of the instant variety, one positioned to show the side having the suture, a second positioned to show the stem cavity, a third positioned to show the apex and a fourth sliced along its longitudinal axis with the pit left in place. A representative twig is also shown in the photograph with the upper sides of characteristic leaves exposed. The lower side of a characteristic leaf is also shown.

DETAILED DESCRIPTION

Referring more specifically to the pomological details of this new and distinct variety of peach tree, the following characteristics were observed under the ecological conditions prevailing at the nursery of H. P. Metzler & Sons at Del Rey, County of Fresno, State of California and is an outlined description thereof. All major color code plate identifications are by reference to the Color Name Chart of the Inter-Society Color Council, National Bureau of Standards.

TREE

Size: Normal.
Vigor: Very vigorous growth.
Productivity: Very good.

Regularity of bearing: Consistently bears well.

Trunk: Normal peach tree trunk with 12 to 14 medium size lenticels per square inch. Color of trunk is normal for peach tree (62-d.g.y. Br.).

Branches: Normal peach tree branches with 12 to 14 medium size lenticels per square inch and of same color as trunk (62-d.g.y. Br.).

Leaves:

*Average length.*—7¼ inches [18.415 cm.] to 7¾ inches [19.685 cm.].

*Average width.*—1½ inches [3.81 cm.] to 1¾ inches [4.445 cm.].

*Shape.*—Lanceolate.

*Margin.*—Serrate.

*Color.*—Upper side (137 d.y.g.). Lower Side (125 d.ol.G.).

*Petiole.*—Approximately ½ inch [1.27 cm.] in length and 1/6 inch [0.4233 cm.] in width.

*Stem glands.*—Reniform. Two of medium size opposed at base of leaf. Color (106 1 01).

Flower buds:

*Size.*—Small ¼ inch [0.635 cm.] in length and 3/16 inch [0.47625 cm.] in diameter.

*Shape.*—Round with stamen showing before bud opens.

Flowers:

*Date of bloom.*—About March 5 to March 9.

*Size.*—¼ inch [0.635 cm.] in length and 3/16 inch [0.47625 cm.] in diameter, each petal.

*Color.*—Dark pink in general. Outer edge of petal (2.S pink). Center of petal (4-1 pink).

FRUIT

Maturity: Reached at Del Rey, in the San Joaquin Valley of California about June 4. Picking date is about four days after the Kern Sun peach tree or about June 1.

Size: Diameter 2½ inches [6.35 cm.] to 3 inches [7.62 cm.]. Average diameter in suture plane about 2¾ inches [6.985 cm.]. Average diameter in plane normal to suture plane about 2¾ inches [6.985 cm.].

Form:

*Uniformity.*—Good.

*Symmetry.*—Good.

*Suture.*—Smooth and very slight extending from base to apex about 3¾ inches [9.525 cm.].

*Ventral surface.*—Rounded to slightly flat.

*Stem cavity.*—Rounded, ¾ inch [1.905 cm.] in diameter and ⅜ inch [0.9525 cm.] in depth.

*Apex.*—Rounded to slightly flat.

*Base.*—Medium wide and flat.

*Pistil point.*—Very small and slightly receded.

Stem:

*Size.*—Length 5/16 inch [0.79375 cm.] and width ⅛ inch [0.3175 cm.].

Skin:

*Thickness.*—Medium.

*Texture.*—Smooth, tough texture and tenacious to flesh.

*Tendency to crack.*—None.

*Pubescense.*—Light.

*Color.*—Dark red (14 v.d. Red) to bright yellow (82 v.y.).

Flesh:

*Color.*—Yellow (83 brill y.).

*Surface of pit cavity.*—Not freestone.

*Color of pit well.*—(83 brill y.).

*Aroma.*—Slight.

*Flavor.*—Mild, very low acid flavor.

*Fibers.*—None.

*Ripening.*—Even.

*Eating quality.*—Good, has mild flavor and low acid taste for an early peach.

Stone:

*Type.*—Not freestone.

*Fibers.*—None.

*Size.*—Length 1⅜ inches [3.4925 cm.], width 1⅛ inches [2.8575 cm.] and thickness 1 1/16 inches [2.69875 cm.].

*Form.*—Normal peach pit, rough with ridges running on longitudinal axes. Stem end flat with slight point at apex. Slight ridge at base with slightly more ridges on top extending from base to apex.

*Color.*—(89 p.y.).

*Ridges.*—Rounded about 1/16 inch [0.15875 cm.] or less in height.

Use: Fresh market.

*Keeping quality.*—Fruit will hold very well on tree and at least three weeks in storage.

*Shipping quality.*—Very good, easy to handle with tight flesh and skin tenacious to flesh.

Although the new variety of peach tree possesses the described characteristics as a result of the growing conditions in Fresno County, Calif., in the central portion of the San Joaquin Valley, it is to be understood that variations of the usual magnitude and characteristics incident to the growing conditions, fertilization, pruning, pest control and other horticultural practices are to be expected.

Having thus described and illustrated my new variety of peach tree, what is claimed as new and desired to be secured by Letters Patent is:

1. A new and distinct variety of peach tree substantially as illustrated and described broadly characterized by its cling fruit having a skin of very high dark red to bright yellow color, very firm yellow flesh having excellent holding quality on the tree, as well as its shipping and storage quality, and ripening for harvest about June 1 and reaching full maturity about June 4 in the San Joaquin Valley of California.

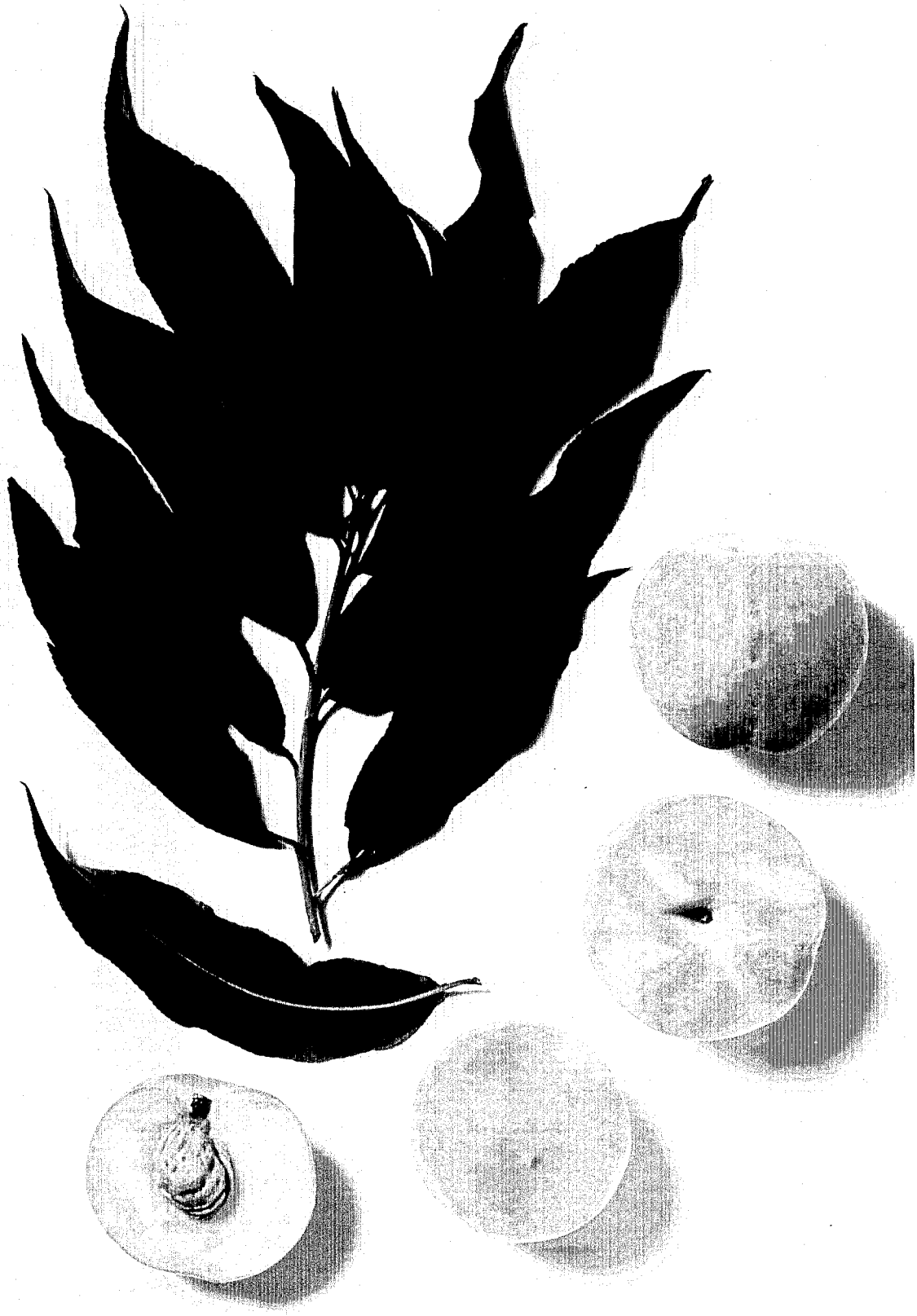

* * * * *